US00PP26658P2

(12) United States Plant Patent
Meinl

(10) Patent No.: US PP26,658 P2
(45) Date of Patent: Apr. 26, 2016

(54) *HYDRANGEA* PLANT NAMED 'SAXREB11'

(50) Latin Name: *Hydrangea macrophylla*
Varietal Denomination: Saxreb11

(71) Applicant: Katrin Meinl, Dresden (DE)

(72) Inventor: Katrin Meinl, Dresden (DE)

(73) Assignee: Kühne Jungpflanzen Claus & Torsten Kühne Gbr, Dresden (DE)

( * ) Notice: Subject to any disclaimer, the term of this patent is extended or adjusted under 35 U.S.C. 154(b) by 94 days.

(21) Appl. No.: 14/120,671

(22) Filed: Jun. 14, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Anne Grunberg
(74) *Attorney, Agent, or Firm* — C. A. Whealy

(57) ABSTRACT

A new and distinct cultivar of *Hydrangea* plant named 'Saxreb11', characterized by its upright and mounded plant habit; moderately vigorous growth habit; strong stems; and large mophead-type inflorescences with dark pink-colored sterile flowers that with aluminum sulfate treatment become bright blue in color.

3 Drawing Sheets

Botanical designation: *Hydrangea macrophylla.*
Cultivar denomination: 'SAXREB11'.

BACKGROUND OF THE INVENTION

The present invention relates to a new and distinct cultivar of *Hydrangea* plant, botanically known as *Hydrangea macrophylla* and hereinafter referred to by the name 'Saxreb11'.

The new *Hydrangea* plant is a product of a planned breeding program conducted by the Inventor in Dresden, Germany. The objective of the breeding program was to develop new container-type *Hydrangea* plants with strong stems, early flowering response and attractive leaf, stem and flower coloration.

The new *Hydrangea* plant originated from a cross-pollination in 2006 of two unidentified proprietary selections of *Hydrangea macrophylla*, not patented. The new *Hydrangea* plant was discovered and selected by the Inventor in 2008 as a flowering plant within the progeny of the stated cross-pollination in a controlled environment in Dresden, Germany.

Asexual reproduction of the new cultivar by softwood cuttings in Dresden, Germany since June, 2008 has shown that the unique features of this new *Hydrangea* plant are stable and reproduced true to type in successive generations of asexual reproduction.

SUMMARY OF THE INVENTION

Plants of the new *Hydrangea* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Saxreb11'. These characteristics in combination distinguish 'Saxreb11' as a new and distinct *Hydrangea* plant:

1. Upright and mounded plant habit.
2. Moderately vigorous growth habit.

3. Strong stems.
4. Large mophead-type inflorescences with dark pink-colored sterile flowers that with aluminum sulfate treatment become bright blue in color.

Plants of the new *Hydrangea* differ primarily from plants of the parent selections in plant habit as plants of the new *Hydrangea* are more compact than plants of the parent selections.

Plants of the new *Hydrangea* can be compared to plants of *Hydrangea macrophylla* 'Horath', disclosed in U.S. Plant Pat. No. 21,291. Plants of the new *Hydrangea* differ primarily from plants of 'Horath' in the following characteristics:

1. Plants of the new *Hydrangea* are more freely branching than plants of 'Horath'.
2. Plants of the new *Hydrangea* and 'Horath' differ in leaf color and luster.
3. Plants of the new *Hydrangea* and 'Horath' differ slightly in sterile flower color.

BRIEF DESCRIPTION OF THE PHOTOGRAPHS

The accompanying colored photographs illustrate the unique appearance of the new *Hydrangea* plant showing the colors as true as it is reasonably possible to obtain in colored reproductions of this type. Colors in the photographs may differ from the color values cited in the detailed botanical description which accurately describe the colors of the new *Hydrangea* plant.

The photograph on the first sheet comprises a side perspective view of a typical flowering plant of 'Saxreb11' grown in a container.

The photograph on the second sheet is a close-up view of a typical inflorescence of 'Saxreb11'.

The photograph on the third sheet is a close-up view of a typical inflorescence of 'Saxreb11' from a plant that was treated with aluminum sulfate.

DETAILED BOTANICAL DESCRIPTION

Plants used in the aforementioned photographs and in the following description were grown in 3-liter containers in a glass-covered greenhouse in Dresden, Germany and under cultural conditions typical of commercial *Hydrangea* production conditions. Plants of the new *Hydrangea* were two years old when the photographs and description were taken. During the production of the plants, day temperatures ranged from 18° C. to 25° C. and night temperatures ranged from 16° C. to 17° C. Some of the plants were treated with aluminum sulfate to "blue" the inflorescences (hereinafter referred to as "blued" plants) and some of the plants were not treated with aluminum sulfate (hereinafter referred to as non-"blued" plants). In the following description, color references are made to The Royal Horticultural Society Colour Chart, 2007 Edition, except where general terms of ordinary dictionary significance are used.

Botanical description: *Hydrangea macrophylla* 'Saxreb11'.

Parentage:

*Female, or seed, parent.*—Unidentified proprietary selection of *Hydrangea macrophylla*, not patented.

*Male, or pollen, parent.*—Unidentified proprietary selection of *Hydrangea macrophylla*, not patented.

Propagation:

*Type cutting.*—By softwood cuttings.

*Time to initiate roots, summer.*—About 16 days at temperatures about 18° C.

*Time to initiate roots, winter.*—About 18 days at temperatures about 18° C.

*Time to produce a rooted young plant, summer.*—About 29 days at temperatures about 18° C.

*Time to produce a rooted young plant, winter.*—About 31 days at temperatures about 18° C.

*Root description.*—Fine, fibrous; white in color.

*Rooting habit.*—Moderately freely branching; sparse.

Plant description:

*Plant and growth habit.*—Perennial subshrub; upright and mounded plant habit; broadly inverted triangle; freely branching habit with about 16 lateral branches developing per plant; strong lateral branches; moderately vigorous growth habit.

*Plant height.*—About 34 cm.

*Plant diameter or area of spread.*—About 53.5 cm.

*Lateral branches.*—Length: About 18.9 cm. Diameter: About 6 mm. Internode length: About 4.2 cm. Texture: Smooth, glabrous. Strength: Strong. Aspect: About 45° from vertical. Color, developing: Close to 143B to 143C slightly tinged with close to N186C at the nodes. Color, developed: Close to 199B to 199C. Lenticels: Density: Sparse. Length: About 2 mm. Diameter: About 1 mm. Color: Close to N186C.

Leaf description:

*Arrangement.*—Opposite, simple.

*Length.*—About 13.3 cm.

*Width.*—About 8.5 cm.

*Shape.*—Ovate.

*Apex.*—Broadly apiculate.

*Base.*—Attenuate.

*Margin.*—Serrate.

*Texture, upper and lower surfaces.*—Glabrous; slightly rugose.

*Venation pattern.*—Pinnate.

*Color.*—Developing leaves, upper surface: Slightly darker than 143A. Developing leaves, lower surface: Close to 146B. Fully expanded leaves, upper surface: Darker than between N137A and 147A; venation, close to 144A to 144B. Fully expanded leaves, lower surface: Close 147B; venation, close to 144B.

*Petioles.*—Length: About 2 cm. Diameter: About 3.5 mm. Texture, upper and lower surfaces: Smooth, glabrous. Color, upper and lower surfaces: Close to 144A.

Inflorescence & flower description:

*Flower type and habit.*—Single sterile and inconspicuous fertile flowers arranged on terminal mophead-type panicles; panicles flattened globular in overall shape; fertile flowers face mostly upright and sterile flowers face upright to outwardly.

*Fragrance.*—Faintly fragrant, pleasant.

*Natural flowering season.*—Continuous flowering from late spring to late summer in The Netherlands.

*Flower longevity, fertile flowers.*—Flowers last about one week on the plant; flowers not persistent.

*Flower longevity, sterile flowers.*—Flowers last about six weeks on the plant; flowers persistent.

*Quantity of flowers.*—Freely flowering; about 90 fertile flowers and about 350 sterile flowers per panicle.

*Panicle height.*—About 11.1 cm.

*Panicle diameter.*—About 18.4 cm.

*Flower diameter, fertile flowers.*—About 8 mm.

*Flower depth (height), fertile flowers.*—About 6 mm.

*Flower diameter, sterile flowers.*—About 3.8 cm.

*Flower depth (height), sterile flowers.*—About 1.3 cm.

*Flower buds, fertile flowers.*—Length: About 4 mm. Diameter: About 3 mm. Shape: Obovate. Color, "blued" flowers: Close to 96D and 97B. Color, non-"blued" flowers: Close to 62B.

*Flower buds, sterile flowers.*—Length: About 9 mm. Diameter: About 6 mm. Shape: Ovoid. Color: Close to 145D.

*Petals, fertile flowers only.*—Quantity and arrangement: Five in a single whorl. Length: About 3 mm. Width: About 1.5 mm. Shape: Ovate, concave. Apex: Acute. Base: Cuneate. Margin: Entire. Texture, upper and lower surfaces: Smooth, glabrous. Color, "blued" plants: When opening and fully opened, upper surface: Close to 100B to 100C. When opening and fully opened, lower surface: Close to 97B to 97C. Color, non-"blued" plants: When opening and fully opened, upper surface: Close to N66C. When opening and fully opened, lower surface: Close to 64D.

*Sepals, fertile flowers.*—Quantity and arrangement: Five in a single whorl. Length: About 1 mm. Width: About 0.1 mm. Shape: Deltoid. Apex: Acute. Base: Broadly cuneate. Margin: Entire. Texture, upper and lower surfaces: Smooth, glabrous. Color: When opening, upper and lower surfaces: Close to 145B to 145C. Fully opened, upper and lower surfaces: Close to 145B to 145C.

*Sepals, sterile flowers.*—Quantity and arrangement: Four or five in a single whorl. Length: About 2.3 cm. Width: About 2.4 cm. Shape: Broadly rhomboidal to broadly ovate. Apex: Bluntly acute. Base: Broadly cuneate. Margin: Entire. Texture, upper and lower surfaces: Smooth, glabrous. Color, "blued" plants: When opening, upper surface: Close to 100C; towards the base, close to 100D. When opening, lower surface: Close to 100D. Fully opened, upper surface: Close to between 97A and 100C; with development, color becoming closer to 97A strongly tinged with close to N88B to N88C. Fully opened, lower surface: Close to 97B; with development, color becoming closer to 97B strongly tinged with close to N88D. Color, non- "blued" plants: When opening, upper surface: Close to 68B. When opening, lower surface: Close to 65A. Fully opened, upper surface: Close to 63B; towards the base, close to 64D; with development, color becoming closer to 64D strongly tined with close to 143B to 143C. Fully opened, lower surface: Close to 65A; with development, color becoming closer to 64D strongly tined with close to 143A.

*Pedicels, fertile flowers.*—Angle: About 20° from vertical. Strength: Moderately strong. Length: About 4 mm. Diameter: About 1 mm. Texture: Smooth, glabrous. Color, "blued" plants: Close to 98C. Color, non-"blued" plants: Close to 70C.

*Pedicels, sterile flowers.*—Angle: About 30° from lateral branch. Strength: Strong. Length: About 2 cm. Diameter: About 1.5 mm. Texture: Smooth, glabrous. Color, "blued" plants: Close to 98B. Color, non-"blued" plants: Close to 64D and marbled with close to 63B.

*Reproductive organs, fertile flowers only.*—Stamens: Quantity per flower: About eight. Filament length: About 3 mm. Filament color: Close to 73B. Anther length: About 0.5 mm. Anther shape: Broadly reniform. Anther color: Close to 185D. Pollen amount: Moderate to abundant. Pollen color: Close to 156D. Pistils: Pistil quantity per flower: About two. Pistil length: About 2.5 mm. Stigma shape: Club-shaped. Stigma color: Close to N155B. Style length: About 2 mm. Style color: Close to 65A to 65B. Ovary color: Close to 157D.

*Seeds and fruits.*—Seed and fruit development have not been observed on plants of the new *Hydrangea* to date.

Disease & pest resistance: Plants of the new *Hydrangea* have not been observed to be resistant to pathogens and pests common to *Hydrangea* plants.

Temperature tolerance: Plants of the new *Hydrangea* have been shown to be tolerant to temperatures in USDA Hardiness Zones 5 to 9.

It is claimed:

1. A new and distinct *Hydrangea* plant named 'Saxreb11' as illustrated and described.

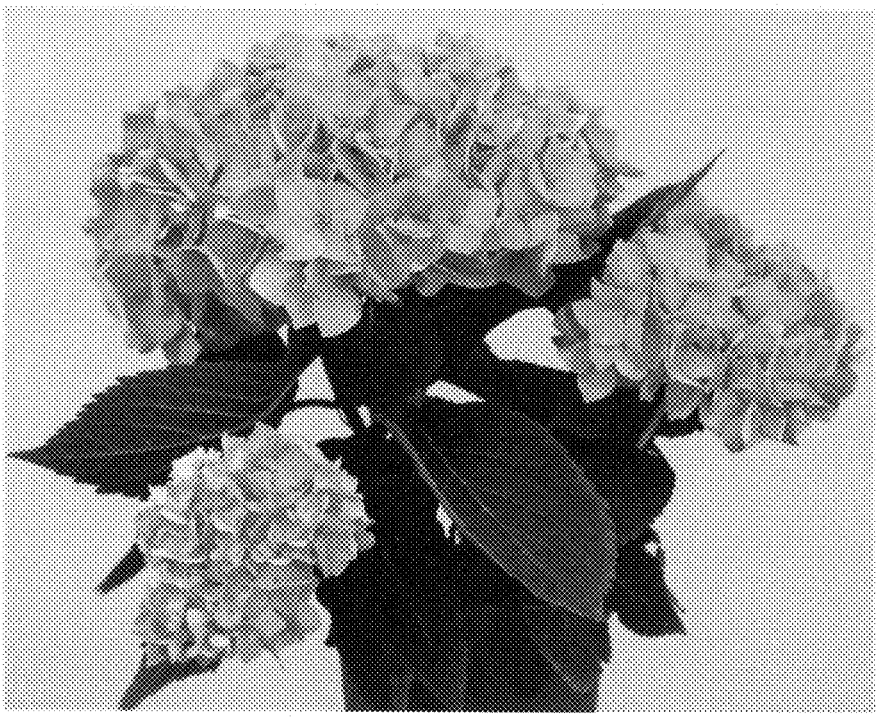

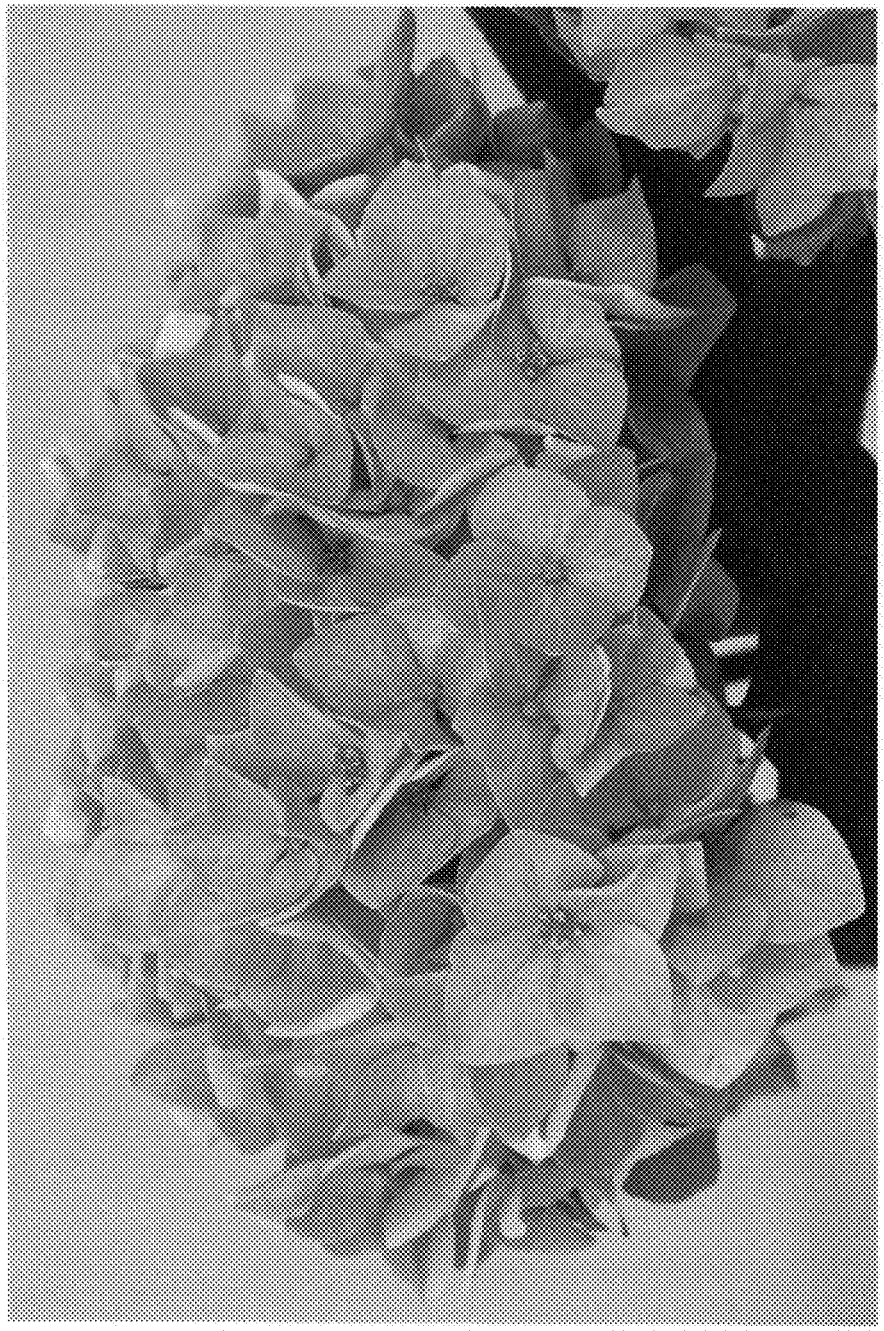

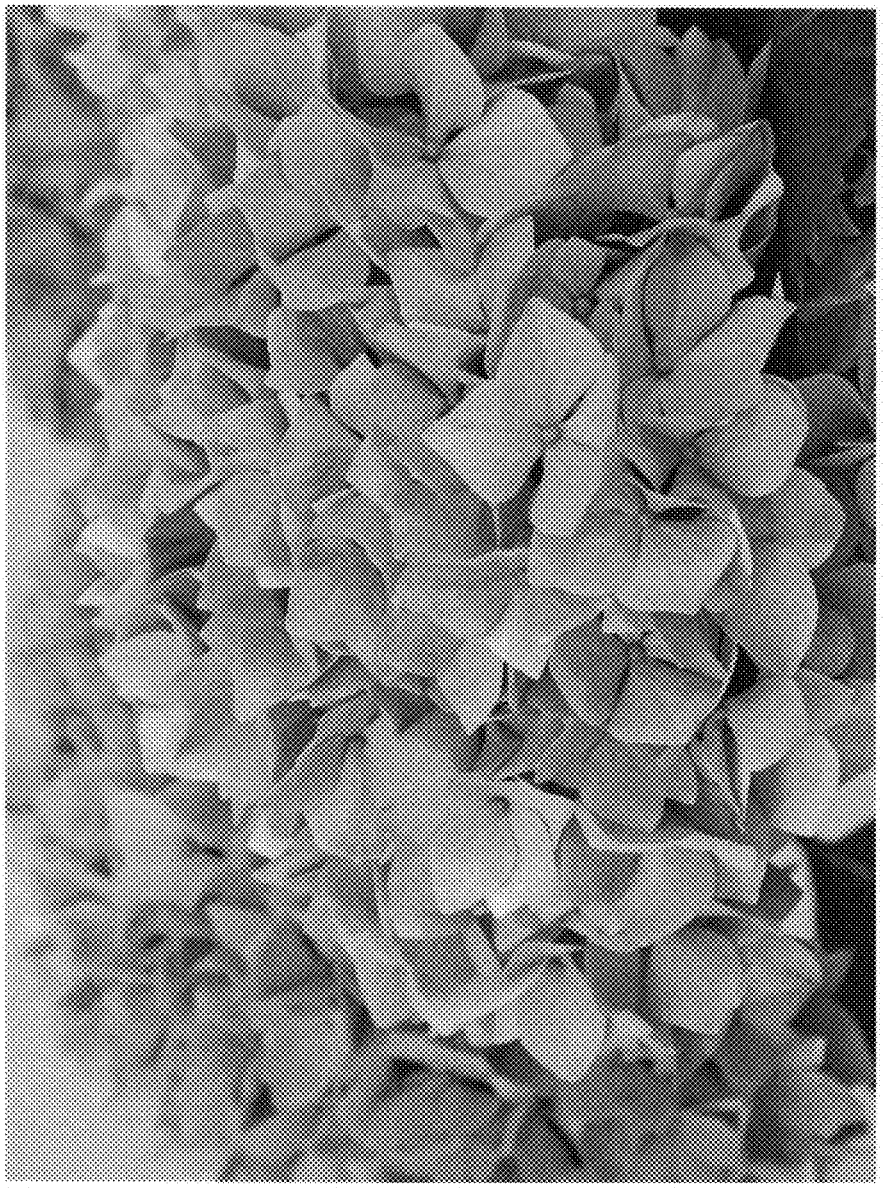

* * * * *